United States Patent
Nauber et al.

(10) Patent No.: US 10,883,958 B2
(45) Date of Patent: Jan. 5, 2021

(54) LIQUID ELECTROLYTE FOR AN ELECTROCHEMICAL GAS SENSOR

(71) Applicant: Dräger Safety AG & Co. KGaA, Lübeck (DE)

(72) Inventors: Andreas Nauber, Stockelsdorf (DE); Michael Sick, Timmendorfer Strand (DE); Gregor Steiner, Titisee-Neustadt (DE); Marie-Isabell Mattern-Frühwald, Bargteheide (DE); Rigobert Chrzan, Bad Oldesloe (DE); Sabrina Sommer, Lübeck (DE); Frank Mett, Lübeck (DE); Andreas Hengstenberg, Reinfeld (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 1093 days.

(21) Appl. No.: 14/890,757

(22) PCT Filed: Sep. 1, 2014

(86) PCT No.: PCT/EP2014/002362
§ 371 (c)(1),
(2) Date: Nov. 12, 2015

(87) PCT Pub. No.: WO2015/032480
PCT Pub. Date: Mar. 12, 2015

(65) Prior Publication Data
US 2016/0116430 A1    Apr. 28, 2016

(30) Foreign Application Priority Data
Sep. 9, 2013 (DE) .......... 10 2013 014 995

(51) Int. Cl.
*G01N 27/404* (2006.01)
*G01N 33/00* (2006.01)

(52) U.S. Cl.
CPC ..... *G01N 27/4045* (2013.01); *G01N 33/0054* (2013.01); *Y02A 50/20* (2018.01)

(58) Field of Classification Search
CPC ............. G01N 27/4045; G01N 27/413; G01N 33/0054
See application file for complete search history.

(56) References Cited

U.S. PATENT DOCUMENTS 4,961,834 A    10/1990  Kuehn et al.
4,997,541 A    3/1991   Kiesele et al.
(Continued)

FOREIGN PATENT DOCUMENTS

DE    10 2008 044 238 A1    6/2010
DE    10 2008 044 239 A1    6/2010
(Continued)

OTHER PUBLICATIONS

Toniolo et al. (J. Electroanal. Chem. 670, 2012, 23-29) (Year: 2012).*
(Continued)

*Primary Examiner* — Maris R Kessel
(74) *Attorney, Agent, or Firm* — McGlew and Tuttle, P.C.

(57) ABSTRACT

A liquid electrolyte, for an electrochemical gas sensor for detecting $NH_3$ or gas mixtures containing $NH_3$, contains at least one solvent, one conductive salt and/or one organic mediator. The conductive salt is an ionic liquid, an inorganic salt, an organic salt or a mixture thereof. The electrolyte preferably is comprised of (I) water, propylene carbonate, ethylene carbonate or a mixture thereof as solvent; (ii) LiCl, KCl, tetrabutylammonium toluenesulphonate or 1-hexyl-3-methylimidazolium tris(pentafluoroethyl)trifluorophosphate as conductive salt; and (iii) tert-butylhydroquinone or anthraquinone-2-sulphonate as organic mediator.

20 Claims, 1 Drawing Sheet

(56) References Cited

U.S. PATENT DOCUMENTS

| | | | |
|---|---|---|---|
| 5,316,648 A | 5/1994 | Kuehn et al. | |
| 2003/0057108 A1* | 3/2003 | Sridharan | A61B 5/14535 |
| | | | 205/775 |
| 2006/0249382 A1 | 11/2006 | Hengstenberg et al. | |
| 2007/0108068 A1* | 5/2007 | Suh | B82Y 30/00 |
| | | | 205/766 |
| 2011/0143225 A1* | 6/2011 | Nakagawa | H01M 4/8605 |
| | | | 429/401 |
| 2011/0226619 A1* | 9/2011 | Eckhardt | G01N 27/401 |
| | | | 204/417 |

FOREIGN PATENT DOCUMENTS

| | | | |
|---|---|---|---|
| DE | 10 2008 044 240 A1 | 6/2010 | |
| EP | 0 221 381 * | 5/1987 | ............ G01N 27/46 |
| EP | 0 395 927 B1 | 1/1993 | |
| EP | 0556558 A2 | 8/1993 | |
| EP | 0 556 558 B1 | 4/2002 | |
| EP | 2 224 018 A1 | 9/2010 | |
| GB | 2 225 859 A | 6/1990 | |
| JP | H02-195247 A | 8/1990 | |
| JP | H02-195248 A | 8/1990 | |
| JP | H09-243594 A | 9/1997 | |
| JP | 2007-240437 A | 9/2007 | |
| JP | 2012-510612 A | 5/2012 | |
| RU | 2011 121 751 A | 1/2013 | |
| RU | 2011 121 754 A | 1/2013 | |
| WO | 95/22055 A1 | 8/1995 | |
| WO | 2010063624 A1 | 6/2010 | |
| WO | 2010063626 A1 | 6/2010 | |
| WO | 2013/045561 A1 | 4/2013 | |
| WO | WO 2013045561 * | 4/2013 | ......... H01M 10/052 |

OTHER PUBLICATIONS

Good et al. (Biochemistry 1966, 5/2, 467-477) (Year: 1966).*
Sigma-Aldrich Goods Buffers (Web link only, created Jul. 2013) (Year: 2013).*
Wikipedia Good's buffers.
Xiaobo Ji et al.: "Determination of ammonia based on the electro-chemical oxidation of N, N'-diphenylenediamine in propylene carbonate", Analytical Sciences, vol. 23, Nov. 2007, pp. 1317-1320, XP055154055.
Giovanelli D et al.: "Determination of ammonia based on the electro-oxidation of hydroquinone in dimethylformamide or in the room temperature ionic liquid, 1-ethyl-3-methylimidazolium bis (trifluoromethylsulfonyl) imide", TALANTA, vol. 62, No. 5, Apr. 2004, pp. 904-911.
Lopez De Mishima B A et al.: "Ammonia sensor based on propylene carbonate", Sensors and Actuators B: Chemical, vol. 131, No. 1, Apr. 14, 2008, pp. 236-240.

* cited by examiner

LIQUID ELECTROLYTE FOR AN ELECTROCHEMICAL GAS SENSOR

CROSS REFERENCE TO RELATED APPLICATIONS

This application is a United States National Phase Application of International Application PCT/EP2014/002362 filed Sep. 1, 2014 and claims the benefit of priority under 35 U.S.C. § 119 of German Patent Application 10 2013 014 995.9 filed Sep. 9, 2013, the entire contents of which are incorporated herein by reference.

FIELD OF THE INVENTION

The present invention pertains to a liquid electrolyte for an electrochemical gas sensor, especially for an electrochemical gas sensor for detecting $NH_3$ or gas mixtures containing $NH_3$.

BACKGROUND OF THE INVENTION

Electrochemical gas sensors, with which the concentration of gaseous ammonia ($NH_3$) can be detected over a limited time period, are generally known. Such sensors are usually used in a great variety of industrial areas, ranging from the chemical industry to agricultural plants via the monitoring of refrigerating systems. They are used especially to recognize critical concentrations of the flammable ammonia gas, which is toxic and corrosive on inhalation and to warn against a corresponding risk.

The electrolyte used in the sensor is one of the essential components of such an electrochemical sensor. The electrolyte is in conductive contact with at least one anode and one cathode. If the gas to be detected enters the electrochemical sensor, a reaction, which leads to a measurable flow of current between the anode and the cathode of the sensor, will typically take place between the gas, the electrolyte and the material of the electrode.

Thus, EP 0 395 927 B1 describes an electrochemical measuring cell for determining ammonia or hydrazine in a gaseous or liquid test sample with at least one measuring electrode and one counterelectrode, which are accommodated in an electrolyte chamber filled with a soluble electrolyte, and which is closed by a permeable membrane towards the test sample.

EP 0 556 558 B1 also provides for an electrochemical measuring cell for determining ammonia, amines, hydrazine and hydrazine derivatives. It is proposed here that a hygroscopic alkali or alkaline earth salt be used as the conductive electrolyte. This shall prevent the drying out of the electrolyte and make possible in this way the most long-term usability possible of the sensor.

The detection of ammonia ($NH_3$) is carried out in electrochemical sensors of such a design by means of an electrochemical reaction between the ammonia gas flowing into the sensor, the electrodes and the electrolyte of the sensor. Entering ammonia gas is oxidized at the measuring electrode in the course of this reaction. The ammonium ions formed in the process are subsequently deprotonated again at the counterelectrode. However, it may prove to be problematic in this connection, for example, that additional nitrogen compounds may be formed as a byproduct of this reaction, which may lead to blocking (poisoning) of the electrode surfaces.

SUMMARY OF THE INVENTION

Based on this, an object of the present invention is to overcome these and other drawbacks of the state of the art.

To accomplish this object, the present invention provides for liquid electrolyte for an electrochemical gas sensor, especially for an electrochemical gas sensor that is suitable for the detection of $NH_3$ or $NH_3$-containing gas mixtures, the present invention makes provisions for the electrolyte to contain at least one solvent, a conductive salt and/or an organic mediator, wherein the conductive salt is an ionic liquid, an inorganic salt, an organic salt or a mixture thereof.

Especially for electrochemical gas sensors, in which electrodes consisting of noble metal or carbon nanotubes are used, such an electrolyte can be used with great advantage to improve the resistance of such a sensor to continuous gas admission. In particular, the risk of a poisoning, as was described above, can be markedly minimized in this way.

It is especially advantageous in this connection if the electrolyte contains a buffer, wherein said buffer is preferably a compound corresponding to

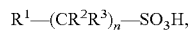

$$R^1-(CR^2R^3)_n-SO_3H, \qquad \text{Formula I}$$

in which n=1, 2, 3, 4 or 5, preferably n=2 or n=3, wherein all $R^2$ and $R^3$ are selected, independently from one another, from among H, NH and OH, and wherein $R^1$ is selected from the group containing piperazinyl, substituted piperazinyl, N-morpholino, cycloalkyl, and tris-(hydroxyalkyl)alkyl. For example, $R^2$ and $R^3$ may be selected, independently from one another, from the group containing piperazinyl, substituted piperazinyl, N-morpholino, cycloalkyl, and tris-(hydroxyalkyl)alkyl. $R^2$ and $R^3$ may be selected, independently from one another, from among H, NH and OH, wherein n=2 and $R^1$ is selected from the group containing N-morpholino and tris-(hydroxyalkyl)alkyl. For example, it is especially advantageous here if n=2 or n=3, wherein all $R^2$ and $R^3$ are selected, independently from one another, from among H, NH and OH, and wherein $R^1$ is selected from among [4-(2-hydroxyethyl)-1]-piperazinyl, (N-morpholino), cyclohexyl, and tris-(hydroxymethyl)methyl. The buffer is especially preferably 3-(N-morpholino)-propanesulfonic acid or 3-(N-morpholino)-ethanesulfonic acid. The electrolyte may be a mixture of a solvent, a conductive salt and/or an organic mediator, wherein the conductive salt is an ionic liquid, an inorganic salt, an organic salt or a mixture thereof, and wherein the electrolyte contains, in addition, especially a buffer, which is selected from among 3-(N-morpholino)-propanesulfonic acid or 3-(N-morpholino)-ethanesulfonic acid.

To prevent the electrolyte from drying out after a certain time, e.g., if the sensor shall be used in continuous operation, it is advantageous, moreover, if the electrolyte contains a component for lowering the vapor pressure as an additional component. The additional component may preferably be an alkylene glycol or polyalkylene glycol, and it is especially preferably propylene glycol, ethylene glycol or a mixture of propylene glycol and ethylene glycol. The electrolyte may be a mixture of a solvent, a conductive salt and/or an organic mediator, wherein the conductive salt is an ionic liquid, an inorganic salt, an organic salt or a mixture thereof, and wherein the electrolyte contains, moreover, at least one alkylene glycol, especially an alkylene glycol, which is selected from among propylene glycol, ethylene glycol or a mixture of propylene glycol and ethylene glycol.

It is favorable, furthermore, if the solvent is selected from the group containing water and alkylene carbonate or mixtures thereof, preferably selected from the group containing water, propylene carbonate, ethylene carbonate or mixtures thereof. The electrolyte may be a mixture of a solvent, a conductive salt and/or an organic mediator, wherein the conductive salt is an ionic liquid, an inorganic salt, an organic salt or a mixture thereof and wherein the solvent is water. As an alternative the electrolyte may be a mixture of a solvent, a conductive salt and/or an organic mediator, wherein the conductive salt is an ionic liquid, an inorganic salt, an organic salt or a mixture thereof and wherein the solvent is alkylene carbonate, especially propylene carbonate, ethylene carbonate or a mixture of propylene carbonate and ethylene carbonate. In this connection, in particular, the electrolyte may be a mixture of a solvent, a conductive salt and/or an organic mediator, wherein the conductive salt is an ionic liquid, an inorganic salt, an organic salt or a mixture thereof, wherein the electrolyte also contains, moreover, a buffer especially a buffer that is selected from among 3-(N-morpholino)-propanesulfonic acid or 3-(N-morpholino)-ethanesulfonic acid and wherein the solvent is alkylene carbonate, especially propylene carbonate, ethylene carbonate or a mixture of propylene carbonate and ethylene carbonate. The electrolyte may be a mixture of a solvent, a conductive slat and/or an organic mediator, wherein the conductive salt is an ionic liquid, an inorganic salt, an organic salt or a mixture thereof, wherein the electrolyte contains, moreover, at least one alkylene glycol, especially an alkylene glycol, which is selected from among propylene glycol, ethylene glycol or a mixture of propylene glycol and ethylene glycol, and wherein the solvent is alkylene carbonate, especially propylene carbonate, ethylene carbonate or a mixture of propylene carbonate and ethylene carbonate.

The anion of the conductive salt is preferably selected from the group containing halides, carbonate, sulfonate, phosphate and/or phosphonate, preferably an anion selected from the group containing alkyl sulfonate, alkenyl sulfonate, aryl sulfonate, alkyl phosphate, alkenyl phosphate, aryl phosphate, substituted alkyl sulfonate, substituted alkenyl sulfonate, substituted aryl sulfonate, substituted alkyl phosphate, substituted alkenyl phosphate, substituted aryl phosphate, halogenated phosphate, halogenated sulfonate, halogenated alkyl sulfonate, halogenated alkenyl sulfonate, halogenated aryl sulfonate, halogenated alkyl phosphate, halogenated alkenyl phosphate, halogenated aryl phosphate, especially preferably an anion selected from the group containing fluorophosphate, alkyl fluorophosphate, aryl sulfonate, and especially preferably from the group containing perfluoroalkyl fluorophosphate and toluene sulfonate.

It is advantageous if the conductive salt contains metal ions, onium ions or mixture of metal ions and onium ions as cations. For example, the metal ions may be selected from among alkali metal ions or alkaline earth metal ions, preferably from among Li, K and/or Na. It is favorable if the onium ions are selected from among ammonium, phosphonium, guanidinium cations and heterocyclic cations, preferably selected from among alkylammonium and heterocyclic cations, especially preferably selected from among alkylammonium, imidazolium and/or substituted imidazolium ions, wherein the substituted imidazolium ions preferably have a structure corresponding to:

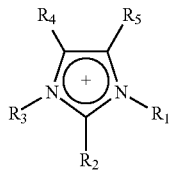

Formula II wherein $R_1$, $R_2$, $R_3$, $R_4$ and $R_5$ may be selected, independently from one another, from among —H, straight-chain or branched alkyl containing 1 to 20 C atoms, straight-chain or branched alkenyl containing 2 to 20 C atoms and one or more double bonds, straight-chain or branched alkinyl containing 2 to 20 C atoms and one or more triple bonds, saturated, partially or fully unsaturated cycloalkyl containing 3-7 C atoms, which may be substituted with alkyl groups containing 1 to 6 C atoms, saturated, partially or fully unsaturated heteroaryl, heteroaryl-C1-C6-alkyl or aryl-C1-C6-alkyl, wherein $R_2$, $R_4$ and $R_5$ are especially preferably H, and $R_1$ and $R_3$ represent each, independently from one another, a straight-chain or branched alkyl containing 1 to 20 C atoms.

In particular, for example, that tetrabutyl ammonium toluene sulfonate or 1-hexyl-3-methylimidazolium-tris(pentafluoroethyl)-trifluorophosphate may be used as the conductive salt. As an alternative the conductive salt is, for example, LiCl, KCl or a mixture of LiCl and KCl. It is thus especially advantageous if the electrolyte is a mixture of a solvent, a conductive salt and/or an organic mediator, wherein the conductive salt is selected from among LiCl, KCl, alkylammonium toluene sulfonate and ionic liquids, with a perfluoroalkyl fluorophosphate anion.

It is favorable, furthermore, if the organic mediator is a polyhydroxy compound, which forms a quinoid system or a naphthalene system during oxidation. For example, the inorganic mediator may be selected from the group containing ortho-dihydroxybenzene, para-dihydroxybenzene, substituted ortho-dihydroxybenzenes and substituted para-dihydroxybenzenes, dihydroxynaphthalene, substituted dihydroxynaphthalene, anthrahydroquinone, substituted anthrahydroquinone, preferably 1,2-dihydroxybenzene, 1,4-dihydroxybenzene, naphthohydroquinone, substituted 1,2- or 1,4-dihydroxybenzene, substituted hydroquinone, substituted naphthohydroquinone, especially preferably substituted anthrahydroquinone, substituted hydroquinone, and substituted 1,2-dihydroxybenzene. It is especially favorable in this connection if the substituents of the substituted anthraquinone, substituted 1,2-dihydroxybenzene and/or substituted 1,4-hydroquinone are selected from the group containing sulfonyl, tert.-butyl, hydroxyl, alkyl, aryl, preferably sulfonic acid and/or tert.-butyl.

It is especially favorable in any case if the electrolyte contains a mixture of propylene carbonate and/or ethylene carbonate as the solvent, LiCl, KCl, tetrabutylammonium toluene sulfonate and/or 1-hexyl-3-methyl-imidazolium tris (pentafluoroethyl)-trifluorophosphate or a mixture of two or more of these components as the conductive salt and tert.-butylhydroquinone and/or a substituted anthraquinone, preferably anthraquinone-2-sulfonate as organic mediator.

The concentration of the organic mediator may be between $10^{-6}$ mol/L and $10^{-2}$ mol/L. Thus, the organic mediator may be contained in the electrolyte at a concentration of $10^{-2}$ mol/L or less, preferably $10^{-3}$ mol/L or less, especially preferably $5·10^{-4}$ mol/L or less, especially preferably $2·10^{-4}$ mol/L or less. The organic mediator may be contained in the electrolyte at a concentration of $10^{-6}$ mol/L or more, preferably $10^{-5}$ mol/L or more, especially preferably $5·10^{-5}$ mol/L or more, especially preferably $8·10^{-5}$ mol/L or more, and especially preferably $10^{-4}$ mol/L or more. In particular, the organic mediator may be present at a concentration of $10^{-5}$ mol/L to $10^{-3}$ mol/L, preferably $5·10^{-5}$ mol/L to $5·10^{-4}$ mol/L, especially preferably $8·10^{-5}$ mol/L to $2·10^{-4}$ mol/L, and especially preferably $10^{-4}$ mol/L.

An electrolyte according to the present invention can be obtained especially preferably by means of a method that comprises the following steps:
a. Charging the solvent into a reaction vessel,
b. Addition of the buffer,
c. Addition of the organic mediator,
d. Heating of the mixture while stirring for about 15 minutes at 150° C.,
e. Stirring for about one hour without further supply of heat until all solids are dissolved,
f. Cooling to room temperature, and
g. Addition of the conductive salt.

Further details and specifics appear from the figures described below and exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
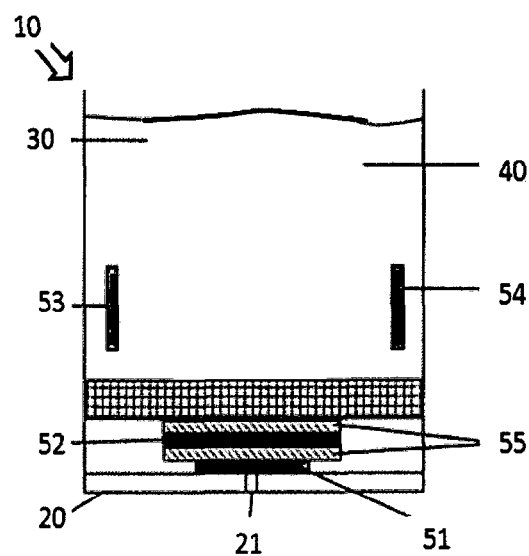
FIG. 1 is a schematic design of an electrochemical gas sensor, with which the electrolyte according to the present invention for detecting ammonia can be used.

FIG. 1 shows an electrochemical gas sensor 10, which has a housing 20 with an electrolyte reservoir 30. A gas inlet 21 and a gas outlet 22 are formed in the housing. A working electrode 51 is arranged within the housing 20 such that the working electrode 51 is in contact with gas that is flowing into the housing 20 through the gas inlet 21. The working electrode 51 is separated from a collecting electrode 52 by means of a glass fiber membrane 55. The collecting electrode 52 is in turn separated from the electrolyte reservoir 30 with a glass fiber membrane 55. Furthermore, a counter-electrode 53 and a reference electrode 54 are arranged within the electrolyte reservoir 30.

The electrolyte 40 according to the present invention is present in the electrolyte reservoir 30. The glass fiber membranes 55 can be impregnated with the electrolyte. The electrolyte 40 can reach in this way both the working electrode 51 and the collecting electrode 52, so that a chemical reaction can take place there corresponding to the scheme shown in FIG. 2 between $NH_3$ flowing in, the material of the working and collecting electrodes 51, 52 and the electrolyte 40.

Figure 2:
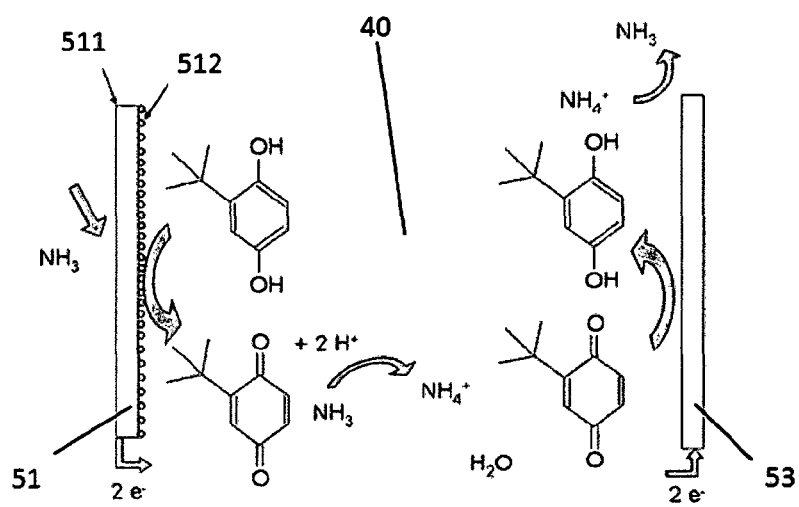
FIG. 2 is a schematic course of a detection reaction for $NH_3$ in an electrochemical gas sensor, which contains an electrolyte according to the present invention.

$NH_3$ flowing into the gas sensor 10 reacts now on the surface of the working electrode 51 with the electrolyte. The working electrode 51 preferably consists, e.g., of a PTFE membrane with a carbon nanotubes coating. The counter-electrode 53 preferably consists of a noble metal. The electrolyte 40 is a composition of propylene carbonate and/or ethylene carbonate as the solvent, 1-hexyl-3-methyl-imidazolium-tris(pentafluoroethyl)-trifluorophosphate as a conductive salt and tert.-butyl-1,2-dihydroxybenzene as the organic mediator in this example. The electrolyte preferably contains, furthermore, a buffer, namely, 3-(N-morpholino)-propanesulfonic acid. As can be seen in FIG. 2, the tert.-butyl-1,2-dihydroxybenzene is oxidized into tert.-butylquinone at the working electrode. The protons released in the process react with the $NH_3$ flowing into the gas sensor 10 into ammonium ions. The ammonium ions reach the counterelectrode 53, where the reverse reaction of the tert.-butylquinone formed previously into 1,2-dihydroxybenzene takes place. $NH_3$, which can escape through the gas outlet 22, is released, in turn, from the ammonium ions. The buffer used stabilizes the pH value of the electrolyte, which is present between the working electrode and the counterelectrode 51, 53 in the electrolyte reservoir 30, in the course of this reaction process.

Exemplary embodiment for preparing an electrolyte according to the present invention:

Polycarbonate is charged as a solvent into a reaction vessel. A 0.4-wt. % buffer, preferably 3-(N-morpholino)-propanesulfonic acid, is added to the polycarbonate. In the next step, 6.9 wt. % of the organic mediator, preferably tert.-butyl-1,2-dihydroxybenzene, are added. The mixture is heated while stirring within 15 minutes, and a maximum temperature of 150° C. is not exceeded. The mixture was subsequently stirred further for one hour without supplying more heat until all solids were dissolved. The solution obtained has a clear, slightly yellowish color.

The solution thus obtained is allowed to stand until it is cooled to room temperature. Then, 2.7 wt. % of the conductive salt, preferably HMIM-FAP (3-hexyl-3-methylimidazolium-tris(pentafluoroethyl)-trifluorophosphte), are added, and the mixture is stirred briefly, for about 1 minute.

While specific embodiments of the invention have been shown and described in detail to illustrate the application of the principles of the invention, it will be understood that the invention may be embodied otherwise without departing from such principles.

The invention claimed is:

1. A liquid electrolyte for an electrochemical gas sensor, the liquid electrolyte comprising:
   at least one solvent;
   a conductive salt and an organic mediator, wherein the conductive salt is an ionic liquid, an inorganic salt, an organic salt or a mixture thereof, the organic mediator being a polyhydroxy compound which forms a quinoid system or a naphthalene system during oxidation, wherein the organic mediator is selected from the group containing substituted ortho-dihydroxybenzenes, substituted paradihydroxybenzenes, dihydroxynaphthalene, substituted dihydroxynaphthalane, anthrahydroquinone, substituted anthrahydroquinone; wherein one of ammonia and ammonia-containing gas mixtures is detected based on at least the liquid electrolyte.

2. An electrolyte according to claim 1, further comprising a buffer, wherein the buffer is a compound corresponding to $$R^1\text{—}(CR^2R^3)_n\text{—}SO_3H, \qquad \text{Formula I}$$

in which n=1, 2, 3, 4 or 5, wherein all $R^2$ and $R^3$ are selected, independently from one another, from among H, NH and OH, and wherein $R^1$ is selected from the group containing piperazinyl, substituted piperazinyl, n-morpholino, cycloalkyl, and tris-(hydroxyalkyl)alkyl.

3. An electrolyte according to claim 2, wherein n=2 or n=3, wherein all $R^2$ and $R^3$ are selected, independently from one another, from among H, NH and OH, and wherein $R^1$ is selected from among [4-(2-hydroxyethyl)-1]-piperazinyl, (N-morpholino), N-cyclohexyl, tris-(hydroxymethyl)methyl, wherein the buffer is 3-(N-morpholino)-propanesulfonic acid or 3-(N-morpholino)-ethanesulfonic acid.

4. An electrolyte according to claim 1, further comprising an additional component for lowering vapor pressure, wherein the additional component is an alkylene glycol or polyalkylene glycol.

5. An electrolyte according to claim 4, wherein the additional component is propylene glycol, ethylene glycol or a mixture of propylene glycol and ethylene glycol.

6. An electrolyte according to claim 1, wherein the solvent is selected from the group containing water and alkylene carbonate or mixtures thereof.

7. An electrolyte according to claim 6, wherein the solvent is selected from the group containing water, propylene carbonate, ethylene carbonate or mixtures thereof.

8. An electrolyte according to claim 1, wherein an anion of the conductive salt is selected from the group containing halides, carbonate, sulfonate, phosphate and/or phosphonate.

9. An electrolyte according to claim 8, wherein the anion is selected from the group containing alkyl sulfonate, alkenyl sulfonate, aryl sulfonate, alkyl phosphate, alkenyl phosphate, aryl phosphate, substituted alkyl sulfonate, substituted alkenyl sulfonate, substituted aryl sulfonate, substituted alkyl phosphate, substituted alkenyl phosphate, substituted aryl phosphate, halogenated phosphate, halogenated sulfonate, halogenated alkyl sulfonate, halogenated alkenyl sulfonate, halogenated aryl sulfonate, halogenated alkyl phosphate, halogenated alkenyl phosphate, and halogenated aryl phosphate.

10. An electrolyte according to claim 8, wherein the anion is selected from the group containing fluorophosphate, alkyl fluorophosphate and aryl sulfonate, perfluoroalkyl fluorophosphate and toluene sulfonate.

11. An electrolyte according to claim 1, wherein the conductive salt contains as cations metal ions, onium ions or a mixture as metal ions and onium ions.

12. An electrolyte according to claim 11, wherein the metal ions are selected from among alkali metal ions or alkaline earth metal ions.

13. An electrolyte according to claim 11, wherein the onium ions are selected from among ammonium, phosphonium and guanidium cations and heterocyclic cations, selected from among alkylammonium and heterocyclic cations, alkylammonium, imidazolium and/or substituted imidazolium ions, wherein substituted imidazolium ions have a structure corresponding to

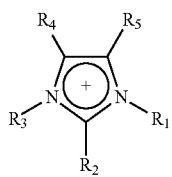

Formula II wherein $R_1$, $R_2$, $R_3$, $R_4$ and $R_5$ may be selected, independently from one another, from among —H, straight-chain or branched alkyl containing 1 to 20 C atoms, straight-chain or branched alkenyl containing 2 to 20 C atoms and one or more double bonds, straight-chain or branched alkinyl containing 2 to 20 C toms and one or more triple bonds, saturated, partially or fully unsaturated cycloalkyl containing 3-7 C atoms, which may be substituted with alkyl groups containing 1 to 6 C atoms, saturated or fully unsaturated heteroaryl, heteroaryl-C1-C6-alkyl or aryl-C1-C6- alkyl, wherein $R_2$, $R_4$ and $R_5$ are H, and $R_1$ and $R_3$ are each, independently from one another, a straight-chain or branched alkyl containing 1 to 20 C atoms.

14. An electrolyte according to claim 1, wherein the organic mediator is selected from the group containing substituted 1,2- or 1,4-dihydroxybenzene, substituted hydroquinone, substituted naphthohydroquinone, substituted anthrahydroquinone, substituted hydroquinone and substituted 1,2-dihydroxybenzene.

15. An electrolyte according to claim 14, wherein the substituents of the substituted anthraquinones, substituted 1,2-dihydroxybenzene and/or substituted 1,4-hydroquinone are selected from the group containing sulfonyl, tert.-butyl, hydroxyl, alkyl, aryl, sulfonic acid and/or tert.-butyl.

16. An electrolyte according to claim 1, wherein the solvent is comprised of a mixture of propylene carbonate and/or ethylene carbonate, and the conductive salt is comprised of one or more of LiCl, KCl, tetrabutylammonium toluene sulfonate and 1-hexyl-3-methylimidazolium tris-(pentafluoroethyl)-trifluorophosphate or a mixture of two or more of these components, and the organic mediator is comprised of tert.-butylhydroquinone and/or a substituted anthraquinone, anthraquinone 2-sulfonate as the organic mediator.

17. An electrolyte according to claim 1, wherein the organic mediator is contained in the electrolyte at a concentration of $10^{-2}$ mol/L or less, preferably $10^{-3}$ mol/L or less.

18. An electrolyte according to claim 1, wherein the organic mediator is contained in the electrolyte at a concentration of $10^{-6}$ mol/L or more.

19. A method, comprising:
preparing an electrolyte, the method comprising the steps of:
charging the solvent into the reaction vessel;
adding the buffer;
adding the organic mediator, the organic mediator being a polyhydroxy compound which forms a quinoid system or a naphthalene system during oxidation, wherein the organic mediator is selected from the group containing substituted ortho-dihydroxybenzenes, substituted paradihydroxybenzenes, dihydroxynaphthalene, substituted dihydroxynaphthalane, anthrahydroquinone, substituted anthrahydroquinone;
heating of the mixture while stirring for about 15 minutes at 150° C.;
stirring for about one hour without further supply of heat until all solids are dissolved;
cooling to room temperature; and
adding the conductive salt;
providing an electrochemical gas sensor comprising the electrolyte;
detecting one of ammonia and ammonia-containing gas mixtures via the electrochemical gas sensor.

20. An electrochemical gas sensor, comprising:
an electrochemical gas sensor structure comprising a liquid electrolyte comprising at least one solvent and a conductive salt and an organic mediator, wherein the conductive salt is an ionic liquid, an inorganic salt, an organic salt or a mixture thereof, the organic mediator being a polyhydroxy compound which forms a quinoid system or a naphthalene system during oxidation, wherein the organic mediator is selected from the group containing substituted ortho-dihydroxybenzenes, substituted paradihydroxybenzenes, dihydroxynaphthalene, substituted dihydroxynaphthalane, anthrahydroquinone, substituted anthrahydroquinone, wherein one of ammonia and ammonia-containing gas mixtures is detected via the electrochemical gas sensor structure.

* * * * *